United States Patent [19]

Stewart

[11] 4,144,137

[45] Mar. 13, 1979

[54] METHOD FOR REMOVAL OF POLYMERIZATION INHIBITOR

[75] Inventor: Thomas Stewart, Andalusia, Pa.

[73] Assignee: Rohm and Haas Company, Philadelphia, Pa.

[21] Appl. No.: 817,777

[22] Filed: Jul. 21, 1977

Related U.S. Application Data

[63] Continuation-in-part of Ser. No. 750,078, Dec. 13, 1976, abandoned.

[51] Int. Cl.$^2$ ............................................. B01D 3/34
[52] U.S. Cl. ................................................... 203/65
[58] Field of Search ............................. 203/6, 7, 8, 65

[56] References Cited

U.S. PATENT DOCUMENTS

| | | | |
|---|---|---|---|
| 3,666,794 | 5/1972 | Otsuki et al. | 203/8 |
| 3,674,651 | 7/1972 | Otsuki | 203/8 |
| 3,794,567 | 2/1974 | Otsuki et al. | 203/8 |
| 3,816,267 | 6/1974 | Chuang | 203/8 |

*Primary Examiner*—Hiram H. Bernstein
*Attorney, Agent, or Firm*—Jordan J. Driks

[57] ABSTRACT

The removal of the polymerization inhibitor p benzoquinone from acrylic and methacrylic monomers is effectuated by adding to the inhibited monomers either prior to distillation or during distillation in a distillation zone, sufficient amounts of a monoalkyl substituted hydroquinone, a 2,5-dialkyl substituted hydroquinone or a dihydroxynaphthalene to prevent the benzoquinone from co-distilling with the monomer or to convert the benzoquinone in a distillation zone to a non-volatile compound during the distillation so that the converted benzoquinone returns to the feed flask.

10 Claims, No Drawings

METHOD FOR REMOVAL OF POLYMERIZATION INHIBITOR

This application is a continuation-in-part of my copending application Ser. No. 750,078 filed Dec. 13, 1976 now abandoned.

This invention relates to a process for removing polymerization inhibitor from acrylic or methacrylic monomers.

Acrylic and methacrylic monomers are routinely processed and stored in the presence of polymerization inhibitors. The useful inhibitors include various phenolic compounds, such as hydroquinone, the monomethyl ether of hydroquinone, benzoquinone, phenol and its derivatives, various amine-containing compounds, such as methylene blue, the phenylenediamines, hydroxylamines, and the like and an assortment of other compounds. Among the commercially significant compounds is p-benzoquinone. This compound is employed to inhibit the polymerization of acrylic and methacrylic monomers during preparation, processing and storage thereof. Although highly effective, p-benzoquinone has a disadvantage in that it is a highly colored quinone which can adversely affect the final monomer product. Thus, it is very often important to have a color-free final product, and this end cannot be achieved with p-benzoquinone present in the monomer. Simple distillation will not result in removal of the p-benzoquinone, since the latter sublimes and co-distills with many acrylic and methacrylic monomers. Accordingly, it has been very difficult to obtain color-free monomers when they have been inhibited with p-benzoquinone.

It has been found, however, that this problem can be overcome by the process of the present invention. It has been found that p-benzoquinone can be readily and completely removed from acrylic and methacrylic monomers by adding thereto, prior to distillation or to the distillation zone during distillation, a compound selected from mono-alkylsubstituted hydroquinones, where the alkyl group has a carbon atom content of $C_1$ - $C_{12}$, preferably $C_6$ - $C_{12}$, 2,5-dialkyl-substituted hydroquinones, where the alkyl groups have a carbon atom content of $C_1$ - $C_8$, preferably $C_3$ - $C_7$, and 1,4-dihydroxynaphthalene, distilling said monomer in a distillation zone, and recovering benzoquinone-free monomer as distillate.

It is postulated that the useful substituted hydroquinones and the dihydroxynaphthalene reduce the p-benzoquinone to hydroquinone, which is a non-volatile compound, while themselves being oxidized to substituted quinones. The substituted quinones resulting from the oxidation are also non-volatile thereby allowing the monomer to be distilled free of both hydroquinone and the substituted quinone.

The useful substituted hydroquinones include mono-alkyl hydroquinones such as toluhydroquinone, mono-t-butylhydroquinone, mono-amyl- and t-amylhydroquinone, mono-octylhydroquinone, monononylhydroquinone, mono-decylhydroquinone and so forth. Also useful are the 2,5-dialkyl hydroquinones, such as the 2,5-dialkyl substituted hydroquinones of the previously mentioned mono-alkyl hydroquinones, for example 2,5-di-t-butylhydroquinone and 2,5-di-t-amylhydroquinone. Equally effective also is 1,4-dihydroxynaphthalene. The preferred compounds are the 2,5-dialkyl-substituted hydroquinones, and most preferred are 2,5-di-t-butyl- and 2,5-di-t-amylhydroquinone. The hydroquinones are used in amounts ranging from 1 to 4 mol equivalents per mol equivalent of p-benzoquinone, with an excess of the hydroquinone over the p-benzoquinone being desirable. Amounts of the substituted hydroquinones in excess of 4 mol equivalents may also be used but there is no particular advantage in using such a large excess. A preferred range is 2 to 3 mol equivalents per mol equivalent of p-benzoquinone.

The acrylic and methacrylic monomers generally inhibited with p-benzoquinone, which can be treated by the process of the invention include acrylic acid and methacrylic acid and alkyl esters thereof, such as butyl acrylate, 2-ethyl-hexyl acrylate, butyl methacrylate, hexyl methacrylate, decyloctyl methacrylate, lauryl methacrylate and so forth.

A significant added benefit of this process is that the substituted quinones formed by the reduction-oxidation reaction have a corrosion inhibiting property. Acrylic and methacrylic acids, especially in crude form and at their boiling points, are highly corrosive to most distillation equipment, even stainless steel 304L. Heretofore, it has been necessary to use equipment made of extremely costly metals, such as Hastelloy ® Alloy C, to carry out the distillations of these acids. The substituted quinones formed during the reduction-oxidation reaction beteen p-benzoquinone and the substituted hydroquinones, however, act as corrosion inhibitors, thereby allowing the acids to be readily distilled in the much less costly stainless steel 304L.

The distillation of the monomers is carried out under conditions normally encountered in such process. Thus, the monomers can be distilled at atmospheric pressure and standard temperatures or at reduced pressures and temperatures. Since inhibitor is being removed, it is manifest that the purified monomer will be very susceptible to polymerization-inducing conditions and influences, and that the uninhibited monomers will have to be rapidly subjected to further processing.

The useful substituted hydroquinones or dihydroxy naphthalene may be added to the flask which contains the material to be distilled. Alternatively, they may be added, during distillation, through a port in a fractionating column.

The fractionating column used is one in which there is a plurality of plates. The vaporized feed wil condense, to a small extent, on these plates and to a much larger extent in a condenser which is vertically arranged and connected to the fractionating column. It is believed that the substituted hydroquinone or dihydroxynaphthalene, when introduced through a port into the fractionating column, reacts almost instantaneously with condensed p-benzoquinone containing monomer. The p-benzoquinone is converted to a non-volatile compound and returns to the feed containing flask and the monomer in the fractionating column continues to be distilled and is collected as a substantially p-benzoquinone free monomer.

If a continuous distillation process is utilized, it is preferable that the feed flask contain a bleed outlet to remove the non-volatiles which collect in the flask as a result of the conversion and removal of p-benzoquinone as a non-volatile.

During a continuous distillation, the feed rate, bleed rate and distillation rate may be adjusted by the operator so that the volume and weight of material in the feed flask will remain substantially constant.

The process for the removal of the p-benzoquinone from acrylic and methacrylic monomers will be more fully understood by reference to the following examples which are included for a better understanding of the invention.

EXAMPLE 1

Batches of glacial acrylic acid inhibited with 1000 ppm of p-benzoquinone are subjected to distillation along with additives to prevent the p-benzoquinone from co-distilling with the acrylic acid. The distillations are carried out using a 1 liter flask with a vapor pipe, in the absence of a distillation column and with the use of a vacuum system. In the absence of a distillation column, the acid is distilled 100% forward with 90% of the charge being taken overhead. A control with no additives is also run. The amount of p-benzoquinone left in the distillate is measured by use of gas liquid chromotography techniques. The results are summarized in Table I.

color of this distillate is determined as greater than fifty using the aforesaid APHA system.

I claim:

1. A process for the removal of polymerization inhibiting p-benzoquinone from an acrylic or methacrylic monomer, which comprises adding thereto, prior to distillation or in a distillation zone during distillation, a compound selected from the group consisting of monoalkyl substituted hydroquinones wherein the alkyl group is attached to the aromatic nucleus and where the alkyl group has a carbon atom content of $C_1$-$C_{12}$, 2,5-dialkyl substituted hydroquinones where the alkyl groups have a carbon atom content of $C_1$-$C_8$, and 1,4-dihydroxynaphthalene, distilling said monomer, or continuing the distillation of said monomer, and recovering p-benzoquinone-free monomer as distillate.

2. The process of claim 1 wherein said compound is added to said monomer during distillation and in the

TABLE I

| | DISTILLATION OF ACRYLIC ACID CONTAINING p-BENZOQUINONE WITH SUBSTITUTED HYDROQUINONES | | | | | | |
|---|---|---|---|---|---|---|---|
| FEED (gm) | CONCENTRATION (ppm) | ADDITIVE | PRESSURE (mm) | POT TEMP. (° C.) | WT. (gm) | COLOR[2] APHA | p-BQ[4] (ppm) |
| 745 + 1000 ppm p-BQ[1] | 0 | — | 30 | 70-90 | 688 | 275 | 420 |
| 700 + 1000 ppm p-BQ | 2960[3] | 1,4-naphthalenediol | 30 | 70-90 | 619 | 20 | <200[5] |
| 700 + 1000 ppm p-BQ | 4630[3] | 2,5-di-t-amyl-hydroquinone | 30 | 70-90 | 579 | 15 | <200[5] |
| 740 + 1000 ppm p-BQ[8] | 4630[3] | " | 30 | 70-90 | 677 | 15 | <200[5] |
| 750 + 1000 ppm p-BQ[9] | 4630[3] | 2,5-di-t-amyl-hydroquinone | 300 | 113 | 599 | 20 | <200[5] |
| 750 + 1000 ppm p-BQ | 2040[3] | toluhydroquinone | 30 | 85-91 | 637 | 130 | — |
| 750 + 1000 ppm p-BQ | 3080[3] | mono-t-butyl-hydroquinone | 30 | 70-90 | 659 | 6 | — |
| 750 + 1000 ppm p-BQ | 4120[3] | 2,5-di-t-butyl-hydroquinone | 30 | 70-90 | 622 | — | <5[7] |
| 750 + 1000 ppm p-BQ | 4970[3] | " | 30 | 70-90 | 638 | — | <5[7] |

[1] p-BQ = p-benzoquinone
[2] The APHA System is a method of measuring the color of fluids. It is a platinum-cobalt scale in which the unit of color is produced by 1 mg. of platinum per liter obtained as a standardized combination of potassium chloroplatinate and cobaltous chloride in graduated concentrations. In this system, a value such as 275 is roughly equivalent to the yellow color commonly seen in legal "yellow" pads. A value of 15-20 is essentially that of colorless water.
[3] 200 mol percent on p-benzoquinone
[4] This is a gas liquid chromotography determination of p-benzoquinone left in the monomer after distillation with the additive.
[5] Indicates lower detectable limits.
[6] Colorless at first, later in distillation some color is brought over.
[7] Determined by high pressure liquid chromotography.
[8] Corrosion rate on stainless steel 304L is nil.
[9] Corrosion rate on stainless steel 304L is .0042 IPY and is uniform.

EXAMPLE 2

Glacial acrylic acid inhibited with 1000 ppm of p-benzoquinone is continuously fed to a flask through a feed inlet. The flask is equipped with a bleed outlet. A twenty plate Oldershaw column equipped with an inlet port is connected to the flask. A condenser is disposed vertically and is connected to the outlet of the Oldershaw column which is remote from the flask. A distillate receiver is connected to the condenser. Glacial acrylic acid is continuously distilled at a pressure of 30 mm, a flask temperature of from 74° to 76° C. and a vapor temperature of 54° to 56° C. 2,5-di-t-hydroquinone is added, during the distillation, through the inlet port of the Oldershaw column in an amount so that the concentration of the 2,5-di-t-amyl-hydroquinone in the feed being distilled, is maintained at a concentration of from 600-700 ppm based on the acrylic acid-p-benzoquinone feed being distilled. During the distillation, the reflux to distillate ratio is maintained at 1:3. Material is, during the distillation, continuously bled from the flask through the bleed outlet. The color of the distillate is determined as less than ten using the APHA system as described in Example 1.

The above procedure is repeated except that no 2,5-di-t-amyl-hydroquinone or other additive is used. The distillation zone.

3. The process of claim 1 where the amount of added compound is from 1 to 4 mol equivalents per mol equivalent of p-benzoquinone.

4. The process of claim 3, where the amount of added compound is from 2 to 3 mol equivalents per mol equivalent of p-benzoquinone.

5. The process of claim 1, where the monomer is acrylic or methacrylic acid.

6. The process of claim 1, where the monomer is an alkyl ester of acrylic or methacrylic acid.

7. The process of claim 1, where the monoalkyl substituted hydroquinone is one selected from the group consisting of toluhydroquinone, mono-t-butylhydroquinone, mono-t-amylhydroquinone, mono-octylhydroquinone and mono-nonylhydroquinone.

8. The process of claim 1, where the 2,5-dialkyl substituted hydroquinone is 2,5-di-t-butyl hydroquinone or 2,5-di-t-amylhydroquinone.

9. The process of claim 1, where the dihydroxynaphthalene is 1,4-naphthalene diol.

10. A process of claim 2, wherein said distillation is continuous and non-volatile components are removed, after formation, from the p-benzoquinone containing monomer.

* * * * *